(12) United States Patent
Hotier et al.

(10) Patent No.: US 6,359,186 B1
(45) Date of Patent: Mar. 19, 2002

(54) PROCESS FOR CO-PRODUCTION OF METAXYLENE AND PARAXYLENE

(75) Inventors: Gérard Hotier, Rueil Malmaison; Larry Mank, Orgeval; Françoise Montecot, Les Clayes sous Bois, all of (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 09/382,577

(22) Filed: Aug. 25, 1999

(30) Foreign Application Priority Data

Aug. 26, 1998 (FR) .............................. 98 10750

(51) Int. Cl.⁷ ................................. C07C 7/12
(52) U.S. Cl. ...................... 585/820; 585/805; 585/822; 585/825
(58) Field of Search ................. 585/805, 820, 585/822, 825

(56) References Cited

U.S. PATENT DOCUMENTS 4,001,111 A * 1/1977 Geissler et al. ............... 210/24
5,284,992 A * 2/1994 Hotier et al. ................ 585/805
5,629,467 A * 5/1997 Hotier et al. ................ 585/805

FOREIGN PATENT DOCUMENTS

EP 0 531 191 3/1993

* cited by examiner

*Primary Examiner*—Walter D. Griffin
*Assistant Examiner*—Tam M. Nguyen
(74) *Attorney, Agent, or Firm*—Millen, White, Zelano & Branigan, P.C.

(57) ABSTRACT

For co-production of metaxylene and paraxylene from a feedstock (line-4) of hydrocarbons, there is employed a simulated moving bed chromatographic column 5 having at least five zones and which delivers an extract, a raffinate and an intermediate raffinate. The feedstock has an ethylbenzene content of less than 5% by weight, and the chromatographic column comprises at least twenty-five beds, of which at least five beds are in zone 3B. The raffinate is distilled (31) to recover the metaxylene at a purity of at least 99% and orthoxylene. The extract is distilled (7, 10) to recover the paraxylene at a purity of at least 99.6%. The recovered isomers can be synthesized into isophthalic acid and terephthalic acid.

22 Claims, 2 Drawing Sheets

PROCESS FOR CO-PRODUCTION OF METAXYLENE AND PARAXYLENE

The invention relates to a process for co-production of paraxylene and metaxylene that comprises in combination 1) a unit for isomerization of the C8-aromatic compounds that dealkylate ethylbenzene, 2) an adsorption unit of a simulated moving bed that has the particular feature of comprising three effluents: an extract that consists of paraxylene and desorbent, an intermediate fraction (extract or raffinate) that contains ethylbenzene with a yield that is close to 100%, a raffinate that contains a mixture of metaxylene and orthoxylene that is substantially free of ethylbenzene and paraxylene, 3) a separation by distillation of orthoxylene from the mixture of metaxylene and orthoxylene.

The production of high-purity paraxylene by separation by adsorption in a simulated moving bed is well known from the prior art. This market is extensively developed; its outlets are the productions of terephthalic acid, phthalic anhydride and terephthalate polyethylene resins. In contrast, the metaxylene market is still restricted, whereby its outlet is isophthalic acid. It was recently perceived that the addition of small amounts of isophthalate polyethylene to terephthalate polyethylene improved the properties of the latter. It therefore becomes advantageous to co-produce paraxylene and metaxylene in the same aromatic compound production complex provided that the market requirements are satisfied: the amount of paraxylene that is produced should be much larger than that of metaxylene: typically 5 to 40 times larger, the paraxylene should be very pure, typically at least 99.6%, and the metaxylene should have reasonable purity, typically at least 99.0%.

The technological background that describes the production of paraxylene with very high purity is illustrated in patent E-PA-531 191 of the applicant.

The prior art knows metaxylene production processes, for example, U.S. Pat No. 4,326,092 where the adsorbent is a zeolite Y of molar ratio Si/Al on the order of 4.5 to 5 exchanged with sodium and where the separation is carried out by the technique of adsorption in a simulated moving bed in liquid phase. In U.S. Pat. No. 5,382,747, the same separation is carried out on a zeolite Y that is exchanged with lithium and sodium, in a restricted range of temperature and degree of hydration by using the toluene as a desorbent. To co-produce the paraxylene in the great majority and metaxylene, the drawback of these processes is to require two separate units of very different sizes, without a possibility of finding any synergy in the co-production of the two isomers.

The prior art also describes processes of co-production of paraxylene and metaxylene; for example, U.S. Pat. No. 4,368,347 uses a vapor phase process with intermediate fraction recycling: in addition to the complication that is linked to recycling of intermediate fractions, this document does not suggest how it is possible to use in a practical way such a process that operates at a pressure of between 1 and 2 bar and at a temperature of 150 to 200° C. with a feedstock whose bubble point is 145° C. and with fixed beds that have pressure drops of at least 0.1 bar and probably more to operate economically. Patent FR 2 651 148 uses two different solvents to separate the C8-aromatic fraction into three effluents, which greatly limits its scope since the distillations that result from the simulated moving bed separation unit are multiplied. Patent WO 93/22022 describes various cases of separations of feedstocks of three components into three effluents, however, the technology. that is used that involves both very high pressures, a pressure regulation and a flow rate regulation in each of the three or four zones of the process and beds that are each separated in a column is justified economically only for products of high added value.

U.S. Pat. No. 4,306,107 describes a simulated moving bed process in liquid phase where the metaxylene is sampled in the form of extract; the paraxylene, orthoxylene and a fraction of ethylbenzene are sampled as an intermediate raffinate; and finally the ethylbenzene is sampled as a raffinate. This process naturally does not allow a majority of paraxylene and an accompanying stream of metaxylene to be co-produced.

The document of the prior art which comes closest to the invention is U.S. Pat. No. 4,313,015; this document describes the separation of a simulated moving bed, in liquid phase, on zeolite X that is exchanged with barium, whereby the desorbent is diethylbenzene. The extract consists of paraxylene that is too impure (99.44%) to be marketed at current standards (current standard=99.6 mini) and with a yield of 97.5%; the intermediate raffinate consists of ethylbenzene, metaxylene and orthoxylene and a little paraxylene; finally the raffinate consists primarily of a mixture of orthoxylene and metaxylene, whereby the metaxylene can be separated by distillation. The text specifies that the intermediate raffinate is sampled approximately in the center of the zone between the introduction point of the feedstock and the sampling point of the raffinate. The feedstock that is dealt with in the example is not completely representative of a feedstock that is found in a refinery: the latter always contain at least traces and sometimes up to 5% paraffins and naphthenes with eight and nine carbon atoms, which distill in the same temperature interval as xylenes. This document does not specify how the paraffins and naphthenes separate between the raffinate and the intermediate raffinate, the total number of beds and the number of beds per zone used, the order of magnitude of the flow rates in each of the zones of the process and more particularly the one in zone 1, therefore the necessary solvent level and the exchange time of the beds (circulation speed of the solid).

The object of the invention is the co-production of paraxylene and metaxylene that can be marketed from a hydrocarbon feedstock that can actually be produced in a refinery. A second object of the invention is to obtain paraxylene with a purity of at least 99.6%, with a minimum yield of 98% and metaxylene with a purity that is at least equal to 99% after distillation. A third object of the invention is to produce, from the same separation unit, substantially more paraxylene than metaxylene (for example at least twice more, for example five times more).

More specifically, the invention relates to a process for co-production of paraxylene and metaxylene from a hydrocarbon feedstock that comprises them, whereby the process comprises a separation stage of said mixture in a simulated moving bed in countercurrent or in co-current in at least one chromatographic column that contains a number of beds of an adsorbent that are interconnected in a closed loop and that have a selectivity that is different for paraxylene, ethylbenzene, metaxylene and orthoxylene, whereby said column comprises at least five zones that are delimited by injections of a feedstock and a desorbent and draw-offs of an intermediate raffinate, a raffinate and an extract, whereby a paraxylene desorption zone 1 is between the injection of the desorbent and the sampling of the extract; a zone 2 for desorption of ethylbenzene, orthoxylene and metaxylene is between the sampling of the extract and the injection of the feedstock; a paraxylene adsorption zone 3A is between the injection of the feedstock and the draw-off of intermediate raffinate; an ethylbenzene adsorption zone 3B is between the draw-off of intermediate raffinate and the draw-off of raffinate; a zone 4 is between the raffinate draw-off and the injection of desorbent, whereby the process is characterized in that:

the feedstock has an ethylbenzene content that is less than 5% by weight, the chromatographic column comprises at least twenty-five beds, of which at least five beds are in zone 3B, the raffinate is distilled at least once to recover metaxylene with a purity of at least 99.0% and orthoxylene and the extract is distilled at least once to recover paraxylene with a purity of at least 99.6%.

Thus, from a complex that comprises a single adsorption unit, with a very high purity, a major ratio of paraxylene and a minor ratio of metaxylene are produced, whereby the metaxylene ratio is obtained with a yield of at least 50%.

In addition, to obtain an economical ortho-metaxylene distillation, it is possible to allow a significant metaxylene fraction to go from the bottom of the distilling column. The recovery level by metaxylene distillation can be at least 50%.

According to a characteristic of the process, the feedstock advantageously can have an ethylbenzene content of less than 2.5% by weight, preferably less than 1.25%. It can also have a content of linear, branched and cyclic alkanes that is less than 1% by weight and advantageously less than 0.1%.

According to a preferred characteristic of the invention, it is possible to inject desorbent into zone 1 and the feedstock into zone 3A of the column in a ratio by weight of desorbent to feedstock of at least 1.8:1, preferably at least 1.9:1.

When this solvent level of at least 1.9:1 is combined with a total number of beds in the column of at least 30 beds, including at least 6 beds in zone 3b, excellent results in terms of purity both in the paraxylene (greater than 99.7) and in the metaxylene (greater than 99.5) and in terms of yield (greater than 98.5 for paraxylene) are obtained.

According to another characteristic, the ratio of flow rates (without desorbent) of raffinate to intermediate raffinate that are drawn off can be less than 0.5 and preferably less than 0.3. As has been described above, the feedstock generally contains less than 5% by weight of ethylbenzene. It can therefore come from either a unit for transalkylation of C7 and C9 into xylenes or a unit for catalytic dismutation of toluene into benzene and xylenes or an isomerization unit of a fluid that contains ethylbenzene, whereby said unit is operated in the presence of a catalyst that dealkylates ethylbenzene into benzene as described in U.S. Pat. No. 5,516,956 and WO 98/05 613 that are incorporated as references, whereby the isomerate that is obtained can be recycled in the unit if it is not adequately dealkylated at the end of a first pass.

After distillation of the desorbent, the intermediate raffinate that contains metaxylene, orthoxylene, ethylbenzene and praraxylene is isomerized in the presence of a preferably dealkylating isomerization catalyst, and the isomerate is recycled at least in part in the adsorption column of a simulated moving bed at the feedstock.

The raffinate that is drawn off at the end of zone 3B contains metaxylene and orthoxylene as well as desorbent. The latter is distilled, and the mixture that contains orthoxylene, once separated by a suitable distillation, is at least in part isomerized as described above and the isomerate that is recycled at least in part at the injection point of the feedstock in the adsorption column.

The recovered desorbent is generally recycled at least in part in the adsorption column at the injection point of the desorbent.

BRIEF DESCRIPTION OF DRAWINGS

The principle of the invention will be better understood from the examination of the figures among which.

DETAILED DESCRIPTION OF DRAWINGS

Figure 1:
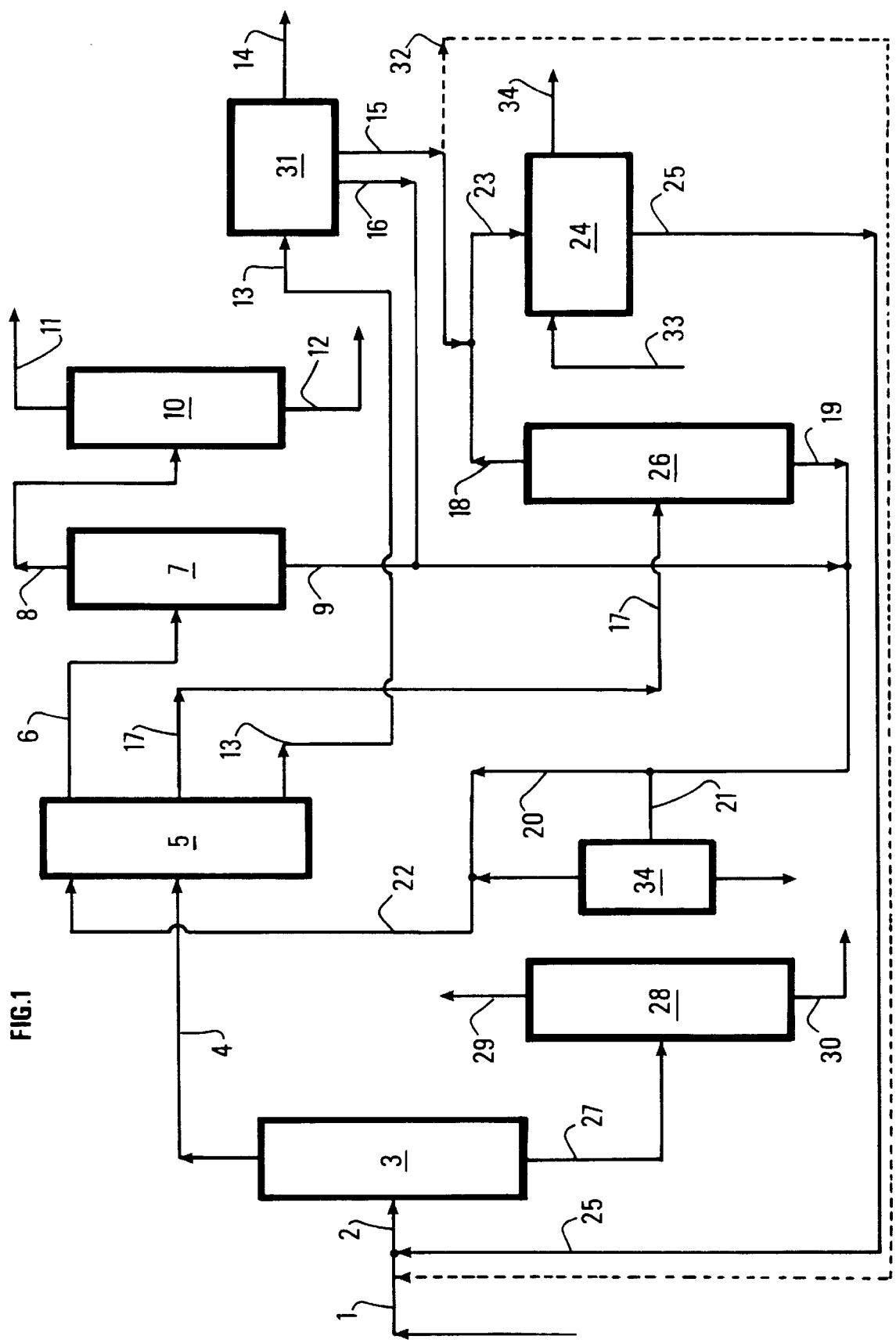
FIG. 1 shows a diagrammatic embodiment of the entire unit for separation of paraxylene and metaxylene in the aromatic loop

According to FIG. 1, a line 1 supplies the entire aromatic loop with fresh feedstock. This fresh feedstock can be obtained either from an aromatizing unit or a unit for dismutation of toluene, or a unit for transalkylation of toluene and C9-aromatic compounds; feedstocks that are too rich in ethylbenzene such as, for example, the pyrolysis gasolines or the steam-cracking effluents, are carefully avoided. The content of paraffins and naphthenes of the fresh feedstock is preferably the lowest possible. An isomerate that is conveyed via a line 25 is added to the fresh feedstock. A line 2 supplies a distilling column 3. Bottom effluent 27 of column 3 can consist essentially of components of C9- and C10-aromatic compounds. Optionally, it can be orthoxylene-rich to be sent into a distilling column 28 to produce purified orthoxylene at the top (line 29) and a mixture of C9- and C10-aromatic compounds at the bottom (line 30). A top effluent 4 of column 3 constitutes the feedstock of a separation unit in a simulated moving bed 5. This feedstock meets the following specifications that are expressed in % by weight: its ethylbenzene content is less than 5%, preferably this content is less than 2.5% and particularly preferably this content is less than 1.25%. Its total content of linear, branched and cyclic alkanes is less than 1%, preferably this content is less than 0.3% and particularly preferably this content is less than 0.1%. The separation unit in a simulated moving bed 5 is supplied, on the one hand, by the feedstock of line 4, and, on the other hand, by desorbent that is conveyed via a line 22. The preferred desorbent is paradiethylbenzene, however, other desorbents such as toluene, paradifluorobenzene or diethylbenzenes in a mixture can also be suitable. The effluents of unit 5 are an extract 6, an intermediate raffinate 17 and a raffinate 13. Extract 6 consists essentially of toluene, paraxylene and desorbent. The intermediate raffinate consists essentially of toluene, metaxylene and orthoxylene, ethylbenzene, paraxylene that is not recovered in the extract and desorbent. Raffinate 13 consists of metaxylene and orthoxylene and desorbent. No separation is observed for the cyclic and non-cyclic alkane between the two raffinates; these components are distributed in proportion to the flow rates of effluents 13 and 17. Extract 6 is sent into a distilling column 7. At the bottom of the column, desorbent that is sent back to lines 20 and 21 is drawn off via a line 9. At the top of the column, a mixture of paraxylene and toluene is drawn off via a line 8. This mixture is sent to a distilling column 10. At the top of the column (line 11), toluene is produced that can be sent back to a unit for disproportionation of toluene into benzene and xylenes or to a transalkylation unit where the toluene reacts with the C9-aromatic compounds to produce xylenes. These units are not shown in FIG. 1. At the bottom of the column, paraxylene of commercial purity, i.e., its paraxylene content is at least 99.6% and preferably said content is greater than 99.7%, is drawn off via a line 12. Raffinate 13 is sent to a unit for separation of metaxylene 31 that is described in FIG. 2. The effluents of unit 31 are the desorbent that is sent back via a line 16 to lines 20 and 21, a mixture that consists essentially of metaxylene and orthoxylene and optionally traces of ethylbenzene that is conveyed via a line 15 to a line 23 and/or via line 32 to line 1 and via line 14, metaxylene of commercial purity, i.e., its metaxylene content is at least 99% and preferably said content is greater than 99.5%. The intermediate raffinate is sent via a line 17 into a distilling column 26. At the bottom of the column, desorbent that is sent back to lines 20 and 21 is drawn off via a line 19, and at the top of the column, a mixture of xylenes and ethylbenzene is drawn off via a line 18. The effluents of line 18 and those of line 15 are sent to isomerization unit 24. This isomerization unit contains a zeolithic catalyst that has the property of dealkylating ethylbenzene into benzene and ethane or into benzene and ethylene; it is generally a zeolite of the family of well known pentasils such as ZSM5, ZSM11, ZSM22. By way of example, the isomerization unit consists of a hydrogen source 33, a reactor, a hydrogen recycling compressor, a high-pressure separator tank and a column for stabilization of the effluent. This type of unit is generally operated at a temperature of between 350 and 500° C., and the hydrogen to hydrocarbon molar ratio is from 1 to 4. The volumetric flow rate in the reactor can be adjusted to increase the yield of the dealkylation reaction of the ethylbenzene to meet the ethylbenzene content specification in line 4. The isomerate is recycled via line 25 to line 1, while the gas effluent (line 34) is sent back either to the gas fuel network or to a unit for separation of hydrogen by PSA-type adsorption. An isomerization unit that would convert ethylbenzene into xylenes usually is not suitable in the process according to the invention primarily because the isomerate would be too rich in naphthenes, such that it would be impossible to separate the metaxylene. The desorbent that is obtained from columns 7, 26 and from unit 31 contains traces of diaromatic products that contain 15 to 20 carbon atoms. A portion of this desorbent (generally from 0.2% to 4%) is conveyed via line 21 to a distilling column 34. These diaromatic products are drawn off at the bottom of this column, and desorbent that is purified via line 22 is drawn off at the top, and said desorbent is added to the bulk of the desorbent (line 20) (not treated) and the recycled desorbent joins unit 5 for separation of xylenes at the introduction point of the desorbent.

Unit 5 for separation of xylenes in a simulated moving bed generally consists of two adsorbers that are filled with molecular sieve X that is exchanged with barium, distributed in 28 beds. Feedstock to be treated arrives via line 4, and said feedstock is supplied sequentially to various beds with all-or-nothing valves 28. Desorbent arrives via line 22, and it is supplied sequentially to various beds with all-or-nothing valves 28. The extract is sampled sequentially from various beds with all-or-nothing valves and evacuated via line 6. The intermediate raffinate is sampled sequentially from various beds with all-or-nothing valves and evacuated via line 17. The raffinate is sampled sequentially from various beds with all-or-nothing valves and evacuated via line 13. Recycling pumps allow the liquid to circulate in the loop that consists of 28 beds. The passage of the liquid from one bed to the next is carried out for the most part by a distributor as described in, for example, the patent (FR 2740053) and for a smaller ratio of typically 2 to 20% by a by-pass line that is described in French application FR 97/16273. The desorbent, extract, feedstock, intermediate raffinate and raffinate are injected and drawn off sequentially in this bypass line.

The particular feature of separation unit 5 is to contain more than 24 beds. According to the invention, it comprises at least twenty-five beds and preferably it comprises at least twenty-eight of them. These beds are distributed in five zones, each of which is to comprises a minimum number of beds to carry out its function.

Between the injection of desorbent and the draw-off of extract, zone 1 has as its object to desorb the paraxylene with desorbent, and this desorption is to be total: more than 0.003% paraxylene will not be tolerated in zone 4; this zone 1 comprises at least four beds and preferably five beds.

Zone 2 is between the draw-off of extract and the introduction of feedstock; it is used to desorb the ethylbenzene and the metaxylene and orthoxylene; it generally comprises at least eight beds and preferably nine beds.

Zone 3A is delimited by the introduction of feedstock and the sampling of intermediate raffinate; its purpose is to ensure the reasonable adsorption of paraxylene; the goal is actually a yield of 95% for example of paraxylene in the extract. According to the invention, this zone comprises at least 5 beds.

Zone 3B is delimited by the sampling of intermediate raffinate and raffinate; this zone has as its object to adsorb at least 96% and preferably at least 98% of the ethylbenzene that is contained in the feedstock, and its second purpose is to finish adsorbing the traces of paraxylene that can be found carried from zone 3A. According to the invention, it generally comprises at least 5 beds.

Zone 4 is delimited by the sampling of raffinate and the injection of desorbent; it ensures the adsorption of metaxylene and orthoxylene and especially the flow rate in this zone is less than the critical value that allows the paraffins and naphthenes to be confined there. It comprises at least two beds and preferably it comprises three beds. The raffinate could be contaminated by paraffins and naphthenes, ethylbenzene or paraxylene, and the invention provides a practical solution for avoiding each of these contaminations. With the selected zeolite absorbing almost none of the linear, branched and cyclic alkanes, no segregation of these components between raffinate and intermediate raffinate is possible. The only method for keeping these components from polluting the raffinate is to very strictly limit their content in the feedstock that is to be treated. This therefore excludes the use in the loop of an isomerization that would convert the ethylbenzene, since this conversion requires working with a balanced concentration in certain naphthenic compounds (intermediate reaction products between ethylbenzene and xylenes). With the difference of adsorption selectivity between ethylbenzene, on the one hand, and the metaxylene and orthoxylene, on the other hand, being very modest (between 1.25/1 and 1.7/1), it is difficult to obtain more than a 98% yield. In a simulated moving bed with 24 beds and four zones that contain a zeolite X that is exchanged with barium, the selectivity between the paraxylene and the ethylbenzene is greater (from 2/1 to 2.3/1) and that between the paraxylene and the metaxylene is much higher (from 3.3/1 to 3.6/1), nevertheless, in a standard way, the number of beds in zone 3 (which influences the paraxylene yield) is from 6 to 8 to obtain yields of 96 to 98.5%. It is therefore clear that if the 7 beds of zone 3 are divided into three and four beds or four and three beds, the paraxylene yield in the extract will inevitably drop: paraxylene will be found in the intermediate raffinate since 3 or 4 beds instead of 7 will be available for carrying out the adsorption of paraxylene. In contrast, the ethylbenzene yield in the intermediate raffinate (carried out by only 4 or 3 beds with a lower selectivity) will be necessarily less than that which is observed for paraxylene. Within the scope of this invention, the goal is first to obtain the minimum commercial purity for the paraxylene or 99.6% and the minimum commercial purity for metaxylene or 99.0%. Preferably, the goal is the best yield possible for the paraxylene or at least 95%. It is impossible to satisfy these three criteria simultaneously without increasing the total number of beds and particularly the number of beds of zone 3. The second criterion of the invention therefore consists in having a simulated moving bed that comprises at least 25 beds and preferably 28 including a total of at least 9 beds and advantageously at least 10 beds for zones 3A and 3B and particularly at least 5 beds in zone 3B. To meet the criterion of purity of the metaxylene in the raffinate, it is especially important to obtain especially low paraxylene contents in this effluent. The paraxylene traces of this effluent can come from two sources—either the liquid that is obtained from zone 3B, and in this case it is within the scope of one skilled in the art to regulate the flow rates in zone 3B and in zone 4 to eliminate this pollution—or the solid that is obtained from zone 1. With the solvent levels that are used conventionally (greater than 1.5), it is possible to desorb from the solid at least a portion of the adsorbed paraxylene. To reduce the content of traces of paraxylene that are contained in the raffinate, it is preferable to increase the solvent level to a value that is greater than 1.8/1 and preferably to a value of at least 1.9/1 and, for example, between 1.9/1 and 2.2/1.

To limit the ethylbenzene content in the raffinate, precautions should be taken on the type of feedstock that is allowed in the aromatic loop. The latter generally has an ethylbenzene content at the input of the separation unit that is less than 5%, for example. A pyrolysis gasoline is not suitable; the better feedstocks are preferably obtained from units for dismutation of toluene or for transalkylation.

Figure 2:
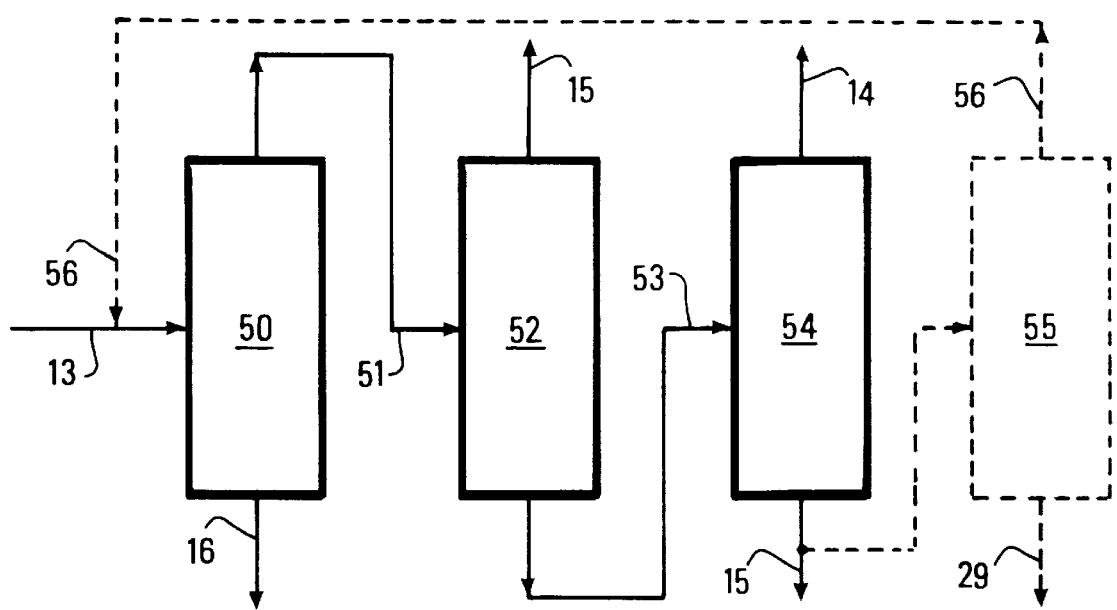
FIG. 2 illustrates a set of distilling columns for the separation of orthoxylene from metaxylene that are contained in the raffinate.

FIG. 2 describes a distilling column train that makes it possible to reduce the ethylbenzene content in the raffinate if this proves necessary, and in any case to remove from metaxylene the orthoxylene that it contains and to produce, if necessary, an additional amount of orthoxylene. Raffinate 13 is allowed in a distilling column 50: desorbent is drawn off at the bottom of the column via line 16, and a mixture of orthoxylene and metaxylene that can contain up to 1% ethylbenzene (depending on the type of fresh feedstock that is allowed in the loop and the yield per pass of the dealkylation of the ethylbenzene in isomerization unit 24) is drawn off via line 51. When the ethylbenzene content of flow 51 is less than 0.3%, it is possible to send it directly to a distilling column 54. If this is not the case, it is necessary to reduce this ethylbenzene flow: it is then sent into a distilling column 52 from which an ethylbenzene-enriched mixture comes out at the top. Typically, this mixture will have an ethylbenzene content of between 0.5 and 10%; it is evacuated via line 15. At the bottom of column 52, an effluent 53 that contains at most 0.2% ethylbenzene comes out. Distilling column 52 is designed to have a number of theoretical trays and a reduced reflux level; it is worked out, for example, that the number of theoretical trays is less than 75 and the reflux level of the column is less than 10 expressed relative to the feedstock; of course, a significant fraction of the metaxylene is lost during this operation. By way of example, a complete separation of the ethylbenzene and the metaxylene would require 300 theoretical trays and a reflux level on the order of 30; the cost of such a separation would of course be prohibitive. The feedstock of distilling column 54 contains less than 0.3% ethylbenzene, 50 to 75% metaxylene and 25 to 50% orthoxylene; its object is to carry out the superfractionation of the metaxylene and orthoxylene. At the top of the column, metaxylene, whose minimum purity is 99.5%, is drawn off via line 14, and at the bottom of the column, a mixture that is low in metaxylene (typically its metaxylene content is 15 to 35%) is drawn off via line 15. There again, the column is calculated to reduce the number of theoretical trays: typically, about 100 theoretical trays will be found in a rectification zone and about 125 theoretical trays will be found in a drainage zone. There again, a significant fraction of metaxylene is lost during this operation. According to the market demand for metaxylene and orthoxylene, it is possible to send the bottom effluent of column 54 to isomerization or to a distilling column 55. At the top of the column, a mixture whose orthoxylene content will be about equal to that of line 13 is drawn off via line 56, and at the bottom of the column, orthoxylene of commercial purity will be drawn off via line 29, there again it is worked out to limit to 200 the number of theoretical trays of this column; this distilling column can be used, for example, to meet exceptional market demands.

The following examples illustrate the invention, among which:

Example 1 (for comparison) describes the treatment of an ethylbenzene-rich feedstock.

Example 2 shows the performance level gain that is obtained by the fact of treating a feedstock that is low in ethylbenzene that is obtained by the union of a dealkylating isomerization and a special fresh feedstock.

Example 3, according to the invention, shows the advantage of going from 24 to 28 beds and of increasing the number of beds in zone 3B, and Example 4 according to the invention shows that the union of a feedstock that is low in ethylbenzene and is treated in a unit with 28 beds that is operated with a solvent level of 1.9/1 makes it possible to obtain excellent results.

EXAMPLE 1

(For Comparison)

An effort is made to reproduce the illustrative description of U.S. Pat. No. 4,313,015 with the molecular sieve and the feedstock that is described in this text and with operating conditions within the scope of one skilled in the art. The pilot unit that is used to do this consists of 24 columns that are 1.1 m in length and 0.021 m in diameter. 344 g of zeolite X that is exchanged with barium with a humidity level of 5.5%, expressed in loss due to fire at 900° C., is charged per column. The operating temperature is 175° C., the pressure in the suction of the recycling pump is kept at 10 bar; all of the injected or draw-off flows are under flow rate monitoring, with the exception of the intermediate raffinate that is under pressure monitoring; the injection and draw-off flow rates are expressed in ambient pressure conditions and at 20° C. The total number of beds is 24. Five beds are counted between the injection of desorbent and the draw-off of raffinate, 8 beds between the draw-off of extract and the injection of feedstock, 4 beds between the injection of feedstock and the draw-off of intermediate raffinate, 4 beds between the draw-off of intermediate raffinate and the draw-off of raffinate and 3 beds between the draw-off of raffinate and the injection of desorbent. 63 cm$^3$/min of feedstock of the composition of 18.6% ethylbenzene, 20.2% paraxylene, 44.7% metaxylene, 16.3% orthoxylene and 0.2% non-aromatic compounds is injected; 101 cm$^3$/min of desorbent that consists of 98.1% paradiethylbenzene and 1.1% metadiethylbenzene is injected, whereby the difference at 100 consists of ten or so components of C10-aromatic compound. 38.65 cm$^3$/min of extract that consists of 0.15% ethylbenzene, 32.1% paraxylene, 0.08% metaxylene, 0.03% orthoxylene, and 66.36% paradiethylbenzene is drawn off, whereby the difference at 100% consists of C10-aromatic compounds. Traces of non-aromatic compounds are not detected; 63.96 cm$^3$/min of intermediate raffinate whose composition is 0.103% non-aromatic compounds, 18.07% ethylbenzene, 0.46% paraxylene, 22.81% metaxylene, 8.31% orthoxylene and 50.26% PDEB is drawn off, whereby the difference at 100% consists of C10-aromatic compounds. 62.354 cm$^3$/min of raffinate whose composition is 0.099% non-aromatic compounds, 0.42% ethylbenzene, 0.045% paraxylene, 22.04% metaxylene, 8.05% orthoxylene and 67.88% PDEB is drawn off, whereby the difference at 100% consists of C10-aromatic compounds. The exchange period is 75 seconds, and the recycling stream mean flow rate is 320 cm$^3$/min expressed at 175° C. This test constitutes the closest result of the prior art.

It is noted that the purity of the paraxylene is only 99.2% instead of 99.45% and mainly that the purity of the metaxylene in the raffinate despite a separation of orthoxylene by allegedly perfect distillation is only 97.5%. U.S. patent application Ser. No. 4,313,015 linked with the knowledge of one skilled in the art do not make it possible to produce a paraxylene fraction and a metaxylene that can be marketed; in contrast, the amount of metaxylene that is produced in comparison with that of paraxylene is much too large, taking into account the market that is to be satisfied.

Example 1 shows that the practice of the prior art within the scope of one skilled in the art makes it possible to obtain neither products of commercial purity nor all of the results that are described in the reference text.

EXAMPLE 2

The pilot unit that is used is the same as that of Example 1; the number of beds in each zone is also identical, and the operating conditions are the same. 63 cm$^3$/min of a feedstock with a composition of 1.14% toluene, 1.67% ethylbenzene, 24.15% paraxylene, 52.33% metaxylene, 20.59% orthoxylene, 0.05% non-aromatic compounds, and 0.092% C9-aromatic compounds is injected. 101 cm$^3$/min of desorbent of a composition that is identical to that of Example 1 is injected. 40.83 cm$^3$/min of extract that consists of 0.97% toluene, 0.012% ethylbenzene, 36.63% paraxylene, 0.08% metaxylene, 0.03% orthoxylene, 0.35% C9-aromatic compounds and 61% paradiethylbenzene is injected, whereby the difference at 100% consists of C10-aromatic compounds. Traces of non-aromatic compounds are not detected. 96.98 cm$^3$/min of intermediate raffinate whose composition is 0.026% non-aromatic compounds, 0.33% toluene, 1.036% ethylbenzene, 0.26% paraxylene, 28.33% metaxylene, 11.15% orthoxylene, 0.35% C9-aromatic compounds and 50.26% PDEB is drawn off, whereby the difference at 100% consists of C10-aromatic compounds. 26.19 cm$^3$/min of raffinate whose composition is 0.026% non-aromatic compounds, 0.01% toluene, 0.16% ethylbenzene, 0.035% paraxylene, 20.84% metaxylene, 8.22% orthoxylene, 0.24% C9-aromatic compounds and 69.4% PDEB is drawn off, whereby the difference at 100% consists of C10-aromatic compounds. The exchange period is 75 seconds, and the recycling stream mean flow rate is 320 cm$^3$/min expressed at 175° C. Relative to Example 1, a clear increase of the purities of the paraxylene in the extract (99.67%) and of metaxylene in the raffinate (98.95% taking into account a perfect distillation of orthoxylene and metaxylene, actually clearly less when an actual distillation is involved) is therefore seen.

EXAMPLE 3
According to the Invention (Variation of the Number of Beds in Zone 3)

The pilot unit that is used is the same as that of Example 1, with the exception that 4 additional beds were added. The number of beds in each zone is distributed in the following manner: zone 1: five beds, zone 2: eight beds, zone 3A: 6 beds, zone 3B: 6 beds, zone 4: 3 beds. 63 cm$^3$/min of feedstock with a composition that is identical to that of Example 2 is injected, and 101 cm$^3$/min of desorbent of a composition that is identical to that of Example 1 is injected. 40.83 cm$^3$/min of extract that consists of 0.97% toluene, 0.006% ethylbenzene, 36.63% paraxylene, 0.08% metaxylene, 0.03% orthoxylene, 0.35% C9-aromatic compounds and 61% paradiethylbenzene is drawn off, whereby the difference at 100% consists of C10-aromatic compounds, and traces of non-aromatic compounds are not detected. 96.98 cm$^3$/min of intermediate raffinate whose composition is 0.026% non-aromatic compounds, 0.33% toluene, 1.066% ethylbenzene, 0.26% paraxylene, 28.33% metaxylene, 11.15% orthoxylene, 0.35% C9-aromatic compounds and 57.61% PDEB is drawn off, whereby the difference at 100% consists of C10-aromatic compounds. 26.19 cm$^3$/min of raffinate whose composition is 0.026% non-aromatic compounds, 0.01% toluene, 0.06% ethylbenzene, 0.035% paraxylene, 20.84% metaxylene, 8.22% orthoxylene, 0.24% C9-aromatic compounds and 69.4% PDEB is drawn off, whereby the difference at 100% consists of C10-aromatic compounds. The exchange period is 75 seconds, and the recycling stream mean flow rate is 320 cm$^3$/min expressed at 175° C. Relative to Example 2, an increase of the purities of the extract (99.69%) and of the raffinate (99.55% taking into account a perfect distillation of the orthoxylene and metaxylene, actually clearly less when an actual distillation is involved) is therefore seen.

EXAMPLE 4
(According to the Invention) Variation of the Solvent Level

The pilot unit that is used is the same as that of Example 3. 63 cm$^3$/min of feedstock with a composition that is identical to that of Examples 2 and 3 is injected; 119.7 cm$^3$/min of desorbent with a composition that is identical to that of Example 1 is injected. 49.49 cm$^3$/min of extract that consists of 0.8% toluene, 0.002% ethylbenzene, 30.28% paraxylene, 0.064% metaxylene, 0.025% orthoxylene, 0.35% C9-aromatic compounds and 67.45% paradiethylbenzene is drawn off, whereby the difference at 100% consists of C10-aromatic compounds, and traces of non-aromatic compounds are not detected. 104.89 cm$^3$/min of intermediate raffinate whose composition is 0.024% non-aromatic compounds, 0.3% toluene, 0.99% ethylbenzene, 0.22% paraxylene, 26.2% metaxylene, 10.3% orthoxylene, 0.35% C9-aromatic compounds and 60.68% PDEB, is drawn off, whereby the difference at 100% consists of C10-aromatic compounds. 28.32 cm$^3$/min of raffinate whose composition is 0.024% non-aromatic compounds, 0.01% toluene, 0.045% ethylbenzene, 0.004% paraxylene, 19.27% metaxylene, 7.6% orthoxylene, 0.35% C9-aromatic compounds, and 71.6% PDEB is drawn off, whereby the difference at 100% consists of C10-aromatic compounds. The exchange period is 75 seconds, and the recycling stream mean flow rate is 320 cm$^3$/min expressed at 175° C. Relative to Example 2, an increase of the purities of the extract (99.7%) and of the raffinate (99.75% taking into account a perfect distillation of the orthoxylene and metaxylene, actually clearly less when an actual distillation is involved) is therefore seen.

EXAMPLE 5
(According to the Invention)

Sent to the input of distilling column 52 is ten t/h of distilled raffinate whose composition is: 0.044% toluene, 0.019% C$_8$-nonaromatic compounds, 0.165% ethylbenzene, 0.076% paraxylene, 71.964% metaxylene, 27.636% orthoxylene, 0.063% C$_9$-non-aromatic compounds and 0.032% C$_9$-aromatic compounds. At the top of the column, 1.495 t/h of distillate whose composition is 0.297% toluene, 0.534% C$_8$-non-aromatic compounds and ethylbenzene, 0.130% paraxylene, 96.248% metaxylene, 2.356% orthoxylene, and 0.308% $C_9$-non-aromatic compounds is drawn off. At the bottom of the column, 8.505 t/h of liquid whose composition is 0.1% ethylbenzene, 0.067% paraxylene, 67.694% metaxylene, 32.081% orthoxylene and 0.02% $C_9$-non-aromatic compounds, and 0.037% $C_9$-aromatic compounds is drawn off. This flow supplies distilling column 54 from which is drawn off at the top 4.36 t/h of distillate that constitutes the commercial metaxylene with composition: 0.185% ethylbenzene, 0.107% paraxylene, 99.579% metaxylene, 0.1% orthoxylene, 0.029% $C_9$-non-aromatic compounds. At the bottom of the column, 4.145 t/h of product with a composition of 0.01% ethylbenzene, 0.02% paraxylene, 34.152% metaxylene, 65.725% orthoxylene, 0.011% $C_9$-non-aromatic compounds, and 0.077% $C_9$-aromatic compounds is drawn off. This bottom product is sent with the top product of column 52 into isomerization. It is therefore noted that in the distilled raffinate, the purity of the initial metaxylene calculated on the C8-aromatic compounds by assuming a perfect separation between the metaxylene and orthoxylene is 99.66%. After the actual distillation train, the purity that is attained is only 99.58% and the commercial metaxylene yield relative to the raffinate is only 60.3%. The commercial metaxylene yield relative to the metaxylene that is contained in the feedstock of the adsorption unit is about 10%. It will be noted that this result is quite far from that of the prior art.

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

The entire disclosure of all applications, patents and publications, cited above and below, and of corresponding French application 98/10.750, are hereby incorporated by reference.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for co-production of paraxylene and metaxylene from a hydrocarbon feedstock mixture, said process comprising separating said mixture in a simulated moving bed countercurrently or co-currently in at least one chromatographic column (5) that contains a plurality of adsorbent beds interconnected in a closed loop and that have a selectivity that is different for paraxylene, ethylbenzene, metaxylene and orthoxylene, said column comprising at least five zones delimited by injections of said hydrocarbon feedstock (4) and a desorbent (22) and draw-offs of an intermediate raffinate (17), a raffinate (13) and an extract (6), withdrawing paraxylene from desorption zone 1 located between the injection of the desorbent and the draw-off of the extract; desorbing ethylbenzene, orthoxylene and metaxylene from desorption zone 2 located between the draw-off of the extract and the injection of the feedstock; adsorbing paraxylene in adsorption zone 3A located between the injection of the feedstock and the draw-off of intermediate raffinate; adsorbing ethylbenzene in adsorption zone 3B located between the draw-off of intermediate raffinate and the draw-off of raffinate; zone 4 is between the raffinate draw-off and the injection of desorbent, wherein:

the feedstock has an ethylbenzene content that is less than 5% by weight, the chromatographic column comprises at least twenty-five beds, the raffinate is distilled at least once to recover metaxylene with a purity of at least 99.0% and orthoxylene, the extract is distilled at least once to recover paraxylene with a purity of at least 99.60%.

2. A process according to claim 1, wherein the feedstock has an ethylbenzene content that is less than 2.5% by weight, and wherein the chromatographic column contains at least twenty-eight beds including at least six in zone 3B.

3. A process according to claim 1, wherein the feedstock has a content of linear, branched and cyclic alkanes that is less than 1% by weight.

4. A process according to claim 1, wherein the desorbent is injected into zone 1 and the feedstock into zone 3A of the column in a ratio by weight of desorbent to feedstock of at least 1.8:1.

5. A process according to claim 1, wherein the ratio of flow rates, aside from desorbent, of raffinate to intermediate raffinate is less than 0.5.

6. A process according to claim 1, wherein the feedstock is obtained from a unit (24) for isomerization of a fluid that is operated in the presence of a dealkylating catalyst.

7. A process according to claim 1, wherein the feedstock is obtained from a unit for dismutation of the toluene that is operated in the presence of a dismutation catalyst.

8. A process according to claim 1, wherein the intermediate raffinate is distilled to remove the desorbent, then isomerized and the isomerate that is obtained is recycled at least in part to the adsorption column.

9. A process according to claim 1, wherein the desorbent and at least in part metaxylene are removed from the raffinate, and wherein the fraction that contains the recovered orthoxylene is isomerized, and the isomerate is at least in part recycled in the adsorption column.

10. A process according to claim 1, wherein the level of recovery by distillation of metaxylene is at least 50%.

11. A process according to claim 2, wherein the ethylbenzene content is less than 1.25%.

12. A process according to claim 3, wherein the content of alkanes is less than 0.1%.

13. A process according to claim 4, wherein said weight ratio of adsorbent to feedstock is at least 1.9:1.

14. A process according to claim 5, wherein said ratio of flow rates is less than 0.3.

15. A process according to claim 1, wherein said feedstock comprises a product from a transalkylation reaction of C7 and C9 into xylenes.

16. A process for co-production of paraxylene and metaxylene from a hydrocarbon feedstock mixture, said process comprising separating said mixture in a simulated moving bed countercurrently or co-currently in at least one chromatographic column (5) that contains a plurality of adsorbent beds interconnected in a closed loop and that have a selectivity that is different for paraxylene, ethylbenzene, metaxylene and orthoxylene, said column comprising at least five zones delimited by injections of said hydrocarbon feedstock (4) and a desorbent (22) and draw-offs of an intermediate raffinate (17), a raffinate (13) and an extract (6), withdrawing paraxylene from desorption zone 1 located between the injection of the desorbent and the draw-off of the extract; desorbing ethylbenzene, orthoxylene and metaxylene from desorption zone 2 located between the draw-off of the extract and the injection of the feedstock; adsorbing paraxylene in adsorption zone 3A located between the injection of the feedstock and the draw-off of intermediate raffinate; adsorbing ethylbenzene in adsorption zone 3B located between the draw-off of intermediate raffinate and the draw-off of raffinate; zone 4 is between the raffinate draw-off and the injection of desorbent, wherein:

the feedstock has an ethylbenzene content that is less than 5% by weight, the chromatographic column comprises at least twenty-five beds, of which at least five beds are in zone 3B.

17. A process for co-production of paraxylene and metaxylene from a hydrocarbon feedstock mixture, said process comprising separating said mixture in a simulated moving bed countercurrently or co-currently in at least one chromatographic column (5) that contains a plurality of adsorbent beds interconnected in a closed loop and that have a selectivity that is different for paraxylene, ethylbenzene, metaxylene and orthoxylene, said column comprising at least five zones delimited by injections of said hydrocarbon feedstock (4) and a desorbent (22) and draw-offs of an intermediate raffinate (17), a raffinate (13) and an extract (6), withdrawing paraxylene from desorption zone 1 located between the injection of the desorbent and the draw-off of the extract; desorbing ethylbenzene, orthoxylene and metaxylene from desorption zone 2 located between the draw-off of the extract and the injection of the feedstock; adsorbing paraxylene in adsorption zone 3A located between the injection of the feedstock and the draw-off of intermediate raffinate; adsorbing ethylbenzene in adsorption zone 3B located between the draw-off of intermediate raffinate and the draw-off of raffinate; zone 4 is between the raffinate draw-off and the injection of desorbent, wherein:

the feedstock has an ethylbenzene content that is less than 5% by weight, the chromatographic column comprises at least twenty-five beds.

18. A process according to claim 17, wherein the feedstock has an ethylbenzene content that is less than 2.5% by weight, and wherein the chromatographic column contains at least twenty-eight beds including at least six in zone 3B.

19. A process according to claim 17, wherein the desorbent is injected into zone 1 and the feedstock into zone 3A of the column in a ratio by weight of desorbent to feedstock of at least 1.8:1.

20. A process according to claim 17, wherein the intermediate raffinate is distilled to remove the desorbent, then isomerized and the isomerate that is obtained is recycled at least in part to the adsorption column.

21. A process according to claim 17, wherein the desorbent an d at least in part metaxylene are removed from the raffinate, and wherein the fraction that contains the recovered orthoxylene is isomerized, and the isomerate is at least in part recycled in the adsorption column.

22. A process according to claim 1, wherein of the at least twenty-five beds in the chromatographic column, at least five beds are in zone 3B.

* * * * *